United States Patent
Celewicz et al.

(10) Patent No.: US 9,260,468 B1
(45) Date of Patent: Feb. 16, 2016

(54) 2,3'-ANHYDRO-2'-DEOXY-5-FLUOROURIDINE DERIVATIVES WITH CYTOTOXIC ACTIVITY, A MANUFACTURING PROCESS AND APPLICATION

(71) Applicant: ADAM MICKIEWICZ UNIVERSITY, Poznań (PL)

(72) Inventors: Lech Celewicz, Poznań (PL); Karol Kacprzak, Pecna (PL); Piotr Ruszkowski, Suchy Las (PL); Marta Lewandowska, Śrem (PL)

(73) Assignee: ADAM MICKIEWICZ UNIVERSITY, Poznañ, (PL)

( * ) Notice: Subject to any disclaimer, the term of this patent is extended or adjusted under 35 U.S.C. 154(b) by 0 days.

(21) Appl. No.: 14/420,487

(22) PCT Filed: Aug. 22, 2014

(86) PCT No.: PCT/PL2014/050050
§ 371 (c)(1),
(2) Date: Feb. 9, 2015

(87) PCT Pub. No.: WO2015/050468
PCT Pub. Date: Apr. 9, 2015

(30) Foreign Application Priority Data

Jul. 24, 2014 (PL) .......................... 408981

(51) Int. Cl.
*C07H 19/10* (2006.01)
(52) U.S. Cl.
CPC ..................... *C07H 19/10* (2013.01)
(58) Field of Classification Search
None
See application file for complete search history.

(56) References Cited

FOREIGN PATENT DOCUMENTS

| WO | 2012/094248 A1 | 7/2012 |
|---|---|---|
| WO | 2012/117246 A1 | 9/2012 |

OTHER PUBLICATIONS

Naveen et al., Bioorganic & Medicinal Chemistry Letters, vol. 20(22), Nov. 2010, pp. 6790-6793.*
Srivastav et al., "Antiviral Activity of 2,3'-Anhydro and Related Pyrimidine Nucleosides Against Hepatitis B Virus," Bioorganic & Medicinal Chemistry Letters, vol. 20, pp. 6790-6793, 2010.
Lewandowska et al., "Synthesis of 3'-Azido-2'-3'-Dideoxy-5-Fluorouidine Phosphoramidates and Evaluation of their Anticancer Activity," European Journal of Medicinal Chemistry, vol. 67, pp. 188-195, 2013.
Vichai et al., "Sulforhodamine B Colorimetric Assay for Cytotoxicity Screening," Nature Protocols, vol. 1, No. 3, pp. 1112-1116.
Oct. 27, 2014 International Search Report issued in International Application No. PCT/PL2014/050050.
Oct. 27, 2014 Written Opinion issued in International Application No. PCT/PL2014/050050.

* cited by examiner

*Primary Examiner* — Traviss C McIntosh, III
(74) *Attorney, Agent, or Firm* — Oliff PLC

(57) ABSTRACT

The subject matter of the invention is novel 2,3'-anhydro-2'-deoxy-5-fluorouridine derivatives of general formula 1

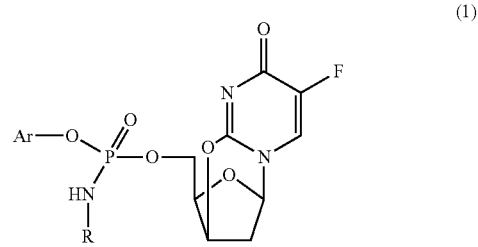

(1)

where R is a trifluoromethyl, 2,2,2-trifluoroethyl, difluoromethyl, perfluoroethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1,2,2-tetrafluoroethyl, 1,2,2,2-tetrafluoroethyl group.
In a second aspect, the subject matter of the invention is a process for the manufacture of 2,3'-anhydro-2'-deoxy-5-fluorouridine derivatives of general formula 1.
In a third aspect, the subject matter of the invention is an application of 2,3'-anhydro-2'-deoxy-5-fluorouridine derivatives of general formula 1 in the anticancer treatment of breast cancer, cervical cancer, lung cancer and nasopharynx cancer.

7 Claims, No Drawings

2,3'-ANHYDRO-2'-DEOXY-5-FLUOROURIDINE DERIVATIVES WITH CYTOTOXIC ACTIVITY, A MANUFACTURING PROCESS AND APPLICATION

The subject matter of the invention is novel 2,3',-anhydro-2'-deoxy-5-fluorouridine derivatives and a process for the manufacture thereof and also their application as cytotoxic agents.

Cancer diseases are one of the principal health disorders reported in humans, having the highest mortality rates and increasing numbers of new cases, primarily related to the increased life expectancy and to lifestyle. The treatment of cancer diseases is difficult, expensive and in many cases not efficacious. Therefore, there is an urgent need for novel substances with cytostatic activity. They may be sourced from natural products and their derivatives as well as constitute synthetic compounds.

Derivatives or analogues of purine or pyrimidine bases and modified nucleosides are a very important group of synthetic cytostatic agents. These include compounds, such as 5-fluorouracil and its derivatives, e.g. 5-fluoro-2'-deoxyuridine (floxuridine). Both 5-fluorouracil and 5-fluoro-2'-deoxyuridine have similar cytostatic activity, and are since many years used in the treatment of cancer, such as breast cancer, gastric cancer, colorectal cancer, ovarian cancer and the like, either in monotherapy or in a combination with other agents. 5-Fluoro-2'-deoxyuridine is also used in the treatment of hepatic cancer owing to better hepatic metabolism compared to 5-fluorouracil. Difficulties with using 5-fluorouracil and 5-fluoro-2'-deoxyuridine are related to the development of cancerous cell resistance to those agents due to their long-term intake. A significant limitation in the use of 5-fluorouracil is its relatively hi\gh toxicity resulted in undesired neurotoxic and cardiotoxic effects. Because 5-fluorouracil and 5-fluoro-2'-deoxyuridine are not selective with respect to cancerous and normal cells, their application in therapy is considerably limited.

As shown by Srivastav, 2,3'-anhydro-2'-deoxy-5-fluorouridine has weak antiviral activity against HBV and negligible cytotoxic activity against the Huh-7 line ($IC_{50}$>200 µg/mL) (Srivastav, M. Mak, B. Agrawal, D. L. J. Tyrrell, R. Kumar Bioorg. Med. Chem. Lett., 2010, 20, 6790-6793).

The objective of the invention has been to develop novel cytotoxic compounds being 2,3'-anhydro-2'-deoxy-5-fluorouridine derivatives showing high selectivity with respect to cancer cells and application thereof in cancer treatment.

The subject matter of the invention is 2,3'-anhydro-2'-deoxy-5-fluorouridine derivatives of general formula 1

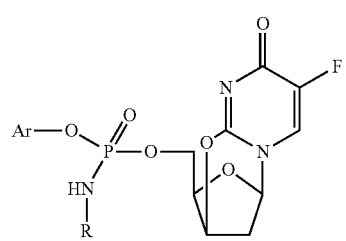

(1)

where:
Ar is a phenyl, 4-chlorophenyl, 1-naphthyl, 2-naphthyl group or a phenyl group substituted at position para, meta or ortho with one F, Cl, Br or I atom, an alkyl substituent containing from 1 to 12 carbon atoms, an alkoxy group containing from 1 to 12 carbon atoms, a nitro or trifluoromethyl group; or a phenyl group substituted at any position with two identical or different substituents of the group of F, Cl, Br or I, an alkyl substituent containing from 1 to 12 carbon atoms, an alkoxy group containing from 1 to 12 carbon atoms, a nitro or trifluoromethyl group;

R is a trifluoromethyl, 2,2,2-trifluoroethyl, difluoromethyl, perfluoroethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1,2,2-tetrafluoroethyl, 1,2,2,2-tetrafluoroethyl group.

In a second aspect, the subject matter of the invention is a process for the manufacture of 2,3'-anhydro-2'-deoxy-5-fluorouridine derivatives of general formula 1

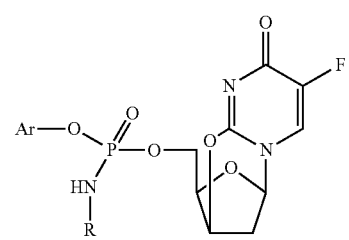

(1)

where Ar and R are as defined above, which involves a reaction of a triazolide of general formula 2, where

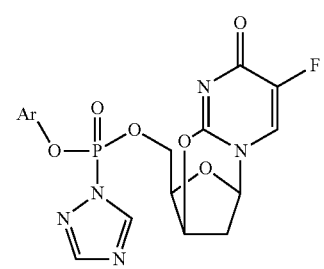

(2)

Ar is a phenyl, 4-chlorophenyl, 1-naphthyl, 2-naphthyl group or a phenyl group substituted at position para, meta or ortho with one F, Cl, Br or I atom, an alkyl substituent containing from 1 to 12 carbon atoms, an alkoxy group containing from 1 to 12 carbon atoms, a nitro or trifluoromethyl group; or a phenyl group substituted at any position with two identical or different substituents of the group of F, Cl, Br or I, an alkyl substituent containing from 1 to 12 carbon atoms, an alkoxy group containing from 1 to 12 carbon atoms, a nitro or trifluoromethyl group;

with fluorinated amines of general formula 3, where

(3)

R is a trifluoromethyl, 2,2,2-trifluoroethyl, difluoromethyl, perfluoroethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1,2,2-tetrafluoroethyl, 1,2,2,2-tetrafluoroethyl group or amine salts of general formula 4,

(4)

where R is as defined above, and X⁻ is an inorganic anion of the group Cl⁻, Br⁻, HSO$_4^-$, SO$_4^{2-}$, NO$_3^-$ in the presence of aliphatic amines, preferably triethylamine.

The reaction starts when a solution containing the triazolide of general formula 2 is treated with fluorinated amine of general formula 3 in a quantity of from 0.1 to 5 equivalents with respect to the triazolide, most preferably 3 equivalents. Alternatively, the reaction of the triazolide of general formula 2 may be carried out with fluorinated amine salts of general formula 4, most preferably with amine hydrochlorides. If so, a solution containing the triazolide is treated with fluorinated aliphatic amine salt of general formula 4 in a quantity of from 0.1 to 5 equivalents with respect to the triazolide, most preferably 3 equivalents, and a tertiary aliphatic amine or pyridine, most preferably triethylamine, in a quantity of from 0.1 to 5 equivalents with respect to the triazolide, most preferably 3 equivalents. The further reaction procedure is identical irrespective of whether an amine of general formula 3 or its salt of general formula 4 is used. The reaction is conducted for 10 minutes to 10 hours, most preferably for 2 hours. The reaction medium is a solvent of the group of lower aliphatic nitriles, anhydrous DMF or DMSO. Most preferably it is acetonitrile. The reaction proceeds at temperatures between 0° C. and 70° C.; due to practical reasons, however, the reaction is most preferably carried out at room temperature. The resulting product is isolated from the reaction mixture by removal of the solvent and purification using column chromatography on silica gel, preferably using a chloroform-methanol mixture as the mobile phase, containing between 0.5% and 50% by volume of methanol, most preferably 1%.

Considering time savings and the commercial availability of reagents, a preferable option for the synthesis of 2,3'-anhydro-2'-deoxy-5-fluorouridine derivatives of general formula 1 is to perform all reactions in single reaction vessel (so called one-pot synthesis). If so, the synthesis consists of three steps carried out one by one so that intermediates do not have to be isolated, according to Scheme 1.

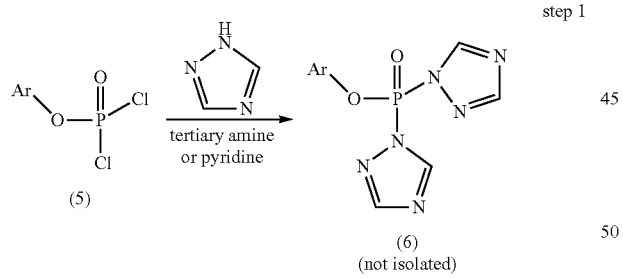

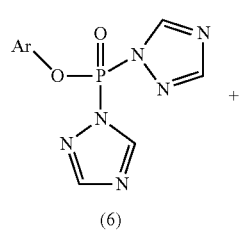

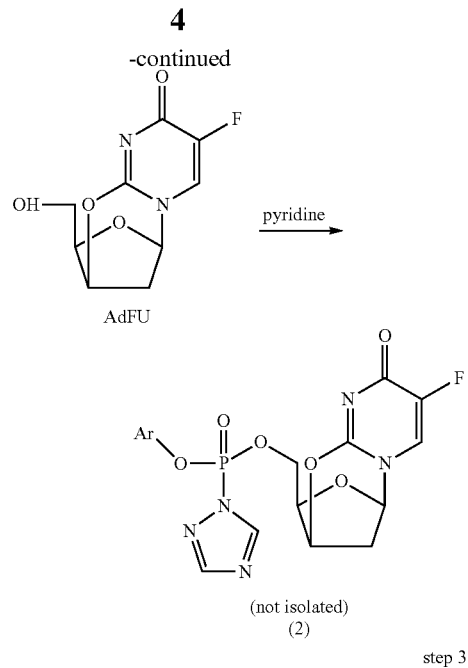

In step 1, an aryldichlorophosphate of general formula 5 is reacted, where Ar is a phenyl, 4-chlorophenyl, 1-naphthyl, 2-naphthyl group or a phenyl group substituted at position para, meta or ortho with one F, Cl, Br or I atom, an alkyl substituent containing from 1 to 12 carbon atoms, an alkoxy group containing from 1 to 12 carbon atoms, a nitro or trifluoromethyl group; or a phenyl group substituted at any position with two identical or different substituents of the group of F, Cl, Br or I, an alkyl substituent containing from 1 to 12 carbon atoms, an alkoxy group containing from 1 to 12 carbon atoms, a nitro or trifluoromethyl group, with 1,2,4-triazole in a quantity of from 2 to 4 equivalents, most preferably three equivalents, in the presence of triethylamine in a quantity of from 2 to 4 equivalents, most preferably 2.5 equivalents, in a solvent of the group of lower aliphatic nitrites, anhydrous DMF or DESO, most preferably in acetonitrile, e.g. following a procedure reported in Lewandowska, M., Ruszkowski, P., Baraniak, D., Czarnecka, A., Kleczewska, N., Celewicz, L. (2013) Eur. J. Med. Chem., 2013, 67, 188-195. This step results in a formation of a bis-triazolide of general formula 6

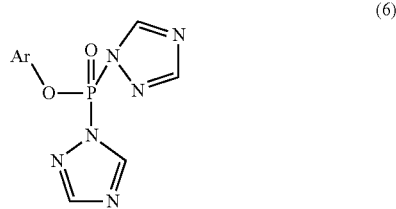

(6)

where Ar is as defined above.

In step 2, the resulting bis-triazolide of general formula 6 is reacted with 2,3'-anhydro-2'-deoxy-5-fluorouridine (AdFU) which forms a triazolide of general formula 2, where Ar is as defined above.

This step is conducted by adding 2,3'-anhydro-2'-deoxy-5-fluorouridine (AdFU) to the reaction mixture in a quantity of from 0.1 to 1 equivalent, most preferably 0.66 equivalent, with respect to the aryldichlorophosphate of general formula 5 used in step 1. An amine, most preferably pyridine, is a necessary additive used in this step which improves AdFU solubility, used in a quantity of from 1 to 3 equivalents with respect to AdFU, most preferably 2 equivalents. The process stage is conducted for 10 minutes to 10 hours, preferably for 3 hours and most preferably for one hour.

In step 3, the triazolide of general formula 2 obtained in step 2 is reacted with fluorinated amines of general formula 3 or salts thereof of general formula 4, most preferably with hydrochlorides, in a presence of triethylamine to yield the final product of general formula 1. This step is conducted by adding a fluorinated amine of general formula 3 to the reaction mixture containing the resulting compound of general formula 2, in a quantity of from 0.1 to 5 equivalents with respect to 2,3'-anhydro-2'-deoxy-5-fluorouridine (AdFU) used in step 2, most preferably 3 equivalents. Alternatively, the reaction of the triazolide of general formula 2 prepared in step 3 may be carried out with fluorinated amine salts of general formula 4, most preferably with hydrochlorides. If so, a fluorinated aliphatic amine salt of general formula 4 is added to a solution containing the triazolide of general formula 2 in a quantity of from 0.1 to 5 equivalents with respect to 2,3'-anhydro-2'-deoxy-5-fluorouridine (AdFU) used in step 2, most preferably 3 equivalents, and a tertiary aliphatic amine or pyridine, most preferably triethylamine, in a quantity of from 0.1 to 5 equivalents with respect to 2,3'-anhydro-2'-deoxy-5-fluorouridine (AdFU), most preferably 3 equivalents. The further reaction procedure is identical irrespective of whether an amine of general formula 3 or its salt of general formula 4 is used. The reaction is conducted for 10 minutes to 10 hours, most preferably for 2 hours at temperatures between 0° C. and 70° C.; due to practical reasons, however, the reaction is most preferably carried out at room temperature. The resulting product is isolated from the reaction mixture by removal of the solvent and purified using column chromatography on silica gel, preferably using a chloroform-methanol mixture as the mobile phase, containing between 0.5% and 50% by volume of methanol, most preferably 1%.

In a third aspect, the subject matter of the invention is an application of 2,3'-anhydro-2'-deoxy-5-fluorouridine derivatives of general formula 1, where Ar is para-chlorophenyl or phenyl and R is —$CF_3$ or —$CF_2$—$CF_3$, in particular 2,3'-anhydro-2'-deoxy-5-fluorouridine 5'-[N-(2,2,2-trifluoroethyl)-O-(4-chlorophenyl)]phosphate—FEAdFU of the invention in the treatment of breast cancer, cervical cancer, lung cancer or nasopharynx cancer. In vitro studies on cancer cell lines of breast cancer, cervical cancer, lung cancer and nasopharynx cancer confirmed strong cytotoxic effects with activity higher than that of 2'-deoxy-5-fluorouridine (5FdU) and 5-fluorouracil already employed in therapy, when tested in identical conditions. Furthermore, FEAdFU has a favourable and high selectivity index (SI) which shows that it has high and selective cytotoxicity against cancer cells with low toxicity against normal cells.

Cytotoxic activity tests were performed using the following cancer cell lines: MCF-7 (breast cancer), HeLa (cervical cancer) A549 (lung cancer) and KB (nasopharynx cancer) and normal cells (human dermal fibroblasts, HDF) obtained from ECACC (European Collection of Cell Cultures).

Cytotoxicity tests were carried out using a standard procedure with sulphorhodamine B. They involved incubation of the cancer cell lines in the logarithmic growth phase for 72 hours with the compound tested and, subsequently, spectrophotometric determination of the degree of cell growth inhibition using adsorption of a dye (sulphorhodamine B) which binds cellular proteins. The determination was carried out according to a procedure reported in: Vichai, V., Kirtikara, K. *Nature Protocols,* 2006, 1, 1112.

Determination of Cytotoxicity

Preparation of Cells for the Experiment:

Cells of the cell line tested in the logarithmic growth phase were seeded onto 24-well plates in a quantity of 20.000 cells/2 mL of the growth medium per well and, subsequently, incubated in an incubator at 37° C., in the 5% $CO_2$ atmosphere for 24 hours.

Solutions of the test compounds were prepared in DMSO in the following concentrations: 0.05; 0.1; 0.5; 1; 5; 10; 50; 100; 500 μM.

The cells of the lines tested were treated with the solutions of the test compounds in a laminar-flow chamber which ensured sterile working conditions according to the following procedure: the first three wells were used as a control: they contained 20 μL of DMSO only; successive solutions of the test compound were added to subsequent wells (20 μL), starting with the lowest concentration (three wells for each concentration level). Subsequently, the plates were placed in an incubator at 37° C. for 72 hours. After the end of incubation, the adhered cells were fixed by adding 500 μL of cold (4° C.) 50% trichloroacetic acid (TCA) and incubated at 4° C. for 1 hour. Subsequently, each well was rinsed with sterile water and dried. The rinsing was repeated five times. The fixed cells were stained for 30 minutes by adding 500 μL of 0.4% dye solution (sulphorhodamine B) dissolved in 1% acetic acid. Any unbound dye was removed by decanting it from the plate, and the cells were washed 4 times with 1% acetic acid. Subsequently, the plates were dried in air for approx. 5 minutes. Bounded dye was dissolved by adding 1500 μL of 10 mM Tris-base buffer (trishydroxymethylaminomethane) to each well and shaken using an orbital shaker for 5 minutes. Subsequently, 200 μL of solution from each well was transferred to each of two wells on a new 96-well plate and absorption of the solutions was determined spectrophotometrically at a wavelength of 490-530 nm using a plate reader. Percentage inhibition of cell growth by the test compound was calculated assuming the absorption of the control solution as 100%.

Cytotoxicity tests for the other compounds and cell lines were performed following an identical procedure.

Depending on the type of the cell line, the following growth media were used:

The MCF-7 line was grown in Dulbecco's Modified Eagle's Medium (DME) from Sigma (cat. no. D5796), while the HeLa, A549 and KB lines were grown in RPMI-1640 Medium from Sigma (cat. no. R8758).

$IC_{50}$ values, being concentration of a compound needed to obtain 50% inhibition of cell growth, were determined for all the derivatives tested. Derivatives for which $IC_{50}$<4 µg/mL are generally assumed as active (abbreviated as A), derivatives with values in an $IC_{50}$ range of 4-30 µg/mL are considered medium active (abbreviated as MA), while those for which $IC_{50}$>30 µg/mL are considered non-active (abbreviated as NA).

To enable comparison, identical tests were performed using known cytotoxic agents: 5-fluoro-2'-deoxyuridine and 5-fluorouracil.

In addition, selectivity indexes (SI) were calculated for FEAdFU, defined as: SI=$IC_{50}$ for a normal cell line (MDF fibroblasts)/$IC_{50}$ for a cancer cell line. A favourable high selectivity index (SI) shows that the activity of a compound against cancer cells is higher than its toxicity against normal cells.

The results of cytotoxic activity tests for the compounds of general formula 1 are shown in Table 1. The values are average results of three independent determinations.

(SI=50) which showed effective activity against cancer cells of that line and low activity against fibroblasts.

In another aspect, the subject matter of the invention is in particular the application of FEAdFU for the manufacture of drugs used in cervical cancer chemotherapy. It was confirmed in the tests that FEAdFU had very high activity against cervical cancer cells (HeLa line), with an $IC_{50}$ of 0.36 µM and more than 36-fold higher cytotoxicity than 5FdU, more than 58-fold higher than 5FU and more than 133-fold higher than AdFU. Furthermore, the compound had a very high selectivity index (SI=33) which showed effective activity against cancer cells of that line and low activity against fibroblasts.

In another aspect, the subject matter of the invention is in particular the application of FEAdFU for the manufacture of drugs used in lung cancer chemotherapy. It was confirmed in the tests performed that FEAdFU had very high activity against lung cancer cells (A549 line), with an $IC_{50}$ of 0.4 µM, and more than 33-fold higher cytotoxicity than 5FdU and more than 53-fold higher than 5FU. Furthermore, the compound had a very high selectivity index (SI=30) which showed effective activity against cancer cells of that line and low activity against fibroblasts.

In the final aspect, the subject matter of the invention is in particular the application of FEAdFU for the manufacture of drugs used in nasopharynx cancer chemotherapy. It was confirmed in the tests that FEAdFU had very high activity against nasopharynx cancer cells (KB line), with an $IC_{50}$ of 0.4 µM, and more than 34-fold higher cytotoxicity than 5FdU, more than 55-fold higher than 5FU and 120-fold higher than AdFU. Furthermore, the compound had a very high selectivity index

TABLE 1

| | Cytotoxic activity, $IC_{50}$ | | | | | | | | | | | | | |
|---|---|---|---|---|---|---|---|---|---|---|---|---|---|---|
| | Line MCF-7 (breast cancer) | | | HeLa (cervical cancer) | | | A549 (lung cancer) | | | KB (nasopharynx cancer) | | | Fibroblasts (HDF) | |
| Compound | [µg/mL] | [µM] | SI | [µg/mL] | [µM] | SI | [µg/mL] | [µM] | SI | [µg/mL] | [µM] | SI | [µg/mL] | [µM] |
| FEAdFU | 0.12 (A) | 0.24 | 50 | 0.18 (A) | 0.36 | 33.3 | 0.2 (A) | 0.4 | 30 | 0.2 (A) | 0.4 | 30 | 6.0 | 12.0 |
| MFEAdFU | 11.8 (MA) | 25.4 | 3.7 | 16.0 (MA) | 34.5 | 2.7 | — | — | — | 12.2 (MA) | 26.3 | 3.5 | 43.1 | 92.9 |
| 2,3'-anhydro-2'-deoxy-5-fluoro uridine (AdFU) | 3.7 (A) | 16.22 | — | 11.0 (MA) | 48.21 | — | — | — | — | 11.0 (MA) | 48.21 | — | — | — |
| 5-fluoro-2'-deoxyuridine | 2.81 (A) | 11.4 | — | 3.20 (A) | 13.0 | — | 3.30 (A) | 13.4 | — | 3.37 (A) | 13.7 | — | — | — |
| 5-fluorouracil | 2.37 (A) | 18.2 | — | 2.73 (A) | 21.0 | — | 2.78 (A) | 21.4 | — | 2.86 (A) | 22.0 | — | — | — |

The cytotoxicity of 2,3'-anhydro-2'-deoxy-5-fluorouridine 5'-[N-(2,2,2-trifluoroethyl)-O-(4-chlorophenyl)]phosphate (FEAdFU) being the subject matter of the application was tested as highly active. Furthermore, the compound has a high selectivity index (SI), defined above, which shows highly selective activity against cancer cells with low activity against normal cells (fibroblasts).

The cytotoxicity and selectivity index of the MFEAdFU derivative, where Ar is para-chlorophenyl and R is —CH$_2$—CH$_2$F, are considerably lower with respect to FEAdFU.

The subject matter of the invention is in particular the application of FEAdFU for the manufacture of drugs used in breast cancer chemotherapy. It was confirmed in the tests that FEAdFU had very high activity against breast cancer cells (MCF-7 line), with an $IC_{50}$ of 0.24 µM and more than 47-fold higher activity than 5FdU and more than 75-fold higher activity than 5FU. It also had 67-fold higher activity than the original 2,3'-anhydro-2'-deoxy-5-fluorouridine (AdFU). Furthermore, the compound had a very high selectivity index (SI=30) which showed effective activity against cancer cells of that line and low activity against fibroblasts.

The subject matter of the invention will be explained using certain embodiments which illustrate the invention, without limiting its scope.

Solvents and other chemical reagents were obtained from Aldrich, Merck and POCh and used as received. Column chromatography was performed with silica gel 60H used as the stationary phase (0.045-0.075 mm/200-300 mesh) from Merck.

$^1$H NMR, $^{13}$C NMR and $^{19}$F NMR spectra of the compounds were recorded using Varian-Gemini (300 MHz) and Bruker Avance (600 MHz) spectrometers with the following internal standards: tetramethylsilane (TMS) when recording

EXAMPLE 1

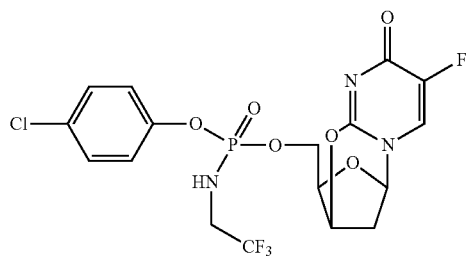

Synthesis of FEAdFU 2,3'-Anhydro-2'-dideoxy-5-fluorouridine (1.07 mmol, 0.244 g) in pyridine (4 mL) was added to a solution of 4-chlorophenyldi(1,2,4-triazole)phosphate (1.07 mmol, 0.332 g) in acetonitrile (4 mL). The reaction was stirred at room temperature for 1 hour; subsequently, 2,2,2-trifluoroethylamine hydrochloride (5.35 mmol, 0.725 g) and triethylamine (2.0 mL) were added to the reaction mixture and the reaction was stirred at room temperature for 1 hour. Reaction progress was monitored using thin-layer chromatography (TLC) with $CHCl_3$/MeOH (10:1) as the eluent. When the substrates were completely consumed, saturated $NaHCO_3$ solution (10 mL) was added to the reaction mixture, followed by extraction with chloroform. The organic phase was dried over anhydrous $MgSO_4$ and evaporated twice with toluene to remove any traces of pyridine. The resulting product was purified on a chromatographic column with silica gel using a chloroform/methanol mixture (100:1, v/v) as the eluent. Yield: 40%.

$^1$H NMR (400 MHz, DMSO-$d_6$): δ 2.33-2.40 (m, 2H, N—$CH_2$); 2.49-2.53 (m, 2H, H-2', H-2"); 3.03 (m, 1H, H-4'); 3.46 (m, 2H, H-5', H-5"); 4.22-4.35 (m, 1H, H-3'); 5.93 (pseudo t, 1H, J=5.8 Hz, H-1'); 6.45 (m, 1H, NH—C—C); 7.23, 7.27 (d, 2H, J=8.7 Hz, 4-ClPh); 7.43, 7.48 (d, 2H, J=8.7 Hz, 4-ClPh); 8.14, 8.17 (d, 1H, J=5.2 Hz, H-6).

$^{13}$C NMR (DMSO-$d_6$): δ31.26, 43.42, 59.38, 77.52, 85.42, 87.34, 122.12, 122.58, 125.59, 129.72, 139.18, 144.27, 149.12, 151.70, 162.93.

$^{19}$F NMR (DMSO-$d_6$): δ −158.26 (d, 1F, J=5.0 Hz); −71.40, −71.36 (t, 3F, J=10.0 Hz, N—C—$CF_3$).

$^{31}$P NMR (DMSO-$d_6$) δ 5.05; 5.20.

MS-ESI m/z: 500, 502 [M+H]$^+$; 522, 524 [M+Na]$^+$; 538, 540 [M+CL]$^-$. 498, 500 [M−H]$^-$; 534, 536, 538 [M+Cl]$^-$.

EXAMPLE 2

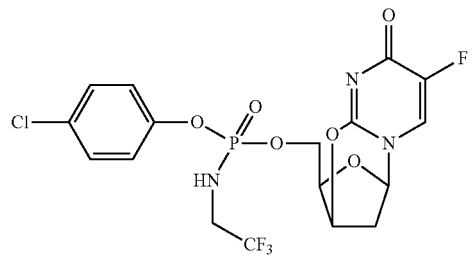

Synthesis of FEAdFU - one-pot procedure 1,2,4-Triazole (5.53 mmol, 0.382 g) and triethylamine (0.62 mL) were added to a solution of 4-chlorophenyldichlorophosphate (1.84 mmol, 0.452 g) in acetonitrile (4.5 mL). The reaction was stirred at room temperature for 30 minutes. After the end of the first step, 2,3'-anhydro-2'-dideoxy-5-fluorouridine (0.88 mmol, 0.200 g) and pyridine (4.5 mL) were added to the reaction mixture. The reaction was stirred at room temperature for 1 hour. Subsequently, 2,2,2-trifluoroethylamine hydrochloride (2.64 mmol, 0.120 g) and triethylamine (1.5 mL) were added to the reaction mixture and the reaction was stirred at room temperature for 2 hours. Reaction progress was monitored using thin-layer chromatography (TLC) with $CHCl_3$/MeOH (10:1) as the eluent. When the substrates were completely consumed, saturated $NaHCO_3$ solution (10 mL) was added to the reaction mixture, followed by extraction with chloroform. The organic phase was dried over anhydrous $MgSO_4$ and evaporated twice with toluene to remove any traces of pyridine. The resulting product was purified on a chromatographic column with silica gel using a chloroform/methanol mixture (100:1, v/v) as the eluent. Yield: 42%.

The product had identical spectral characteristics as that discussed in Example 1.

EXAMPLE 3

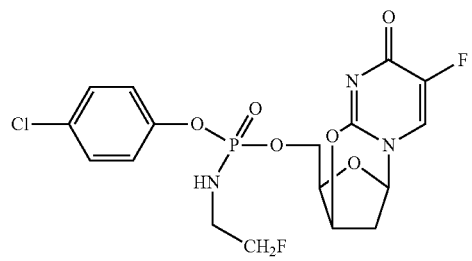

Synthesis of MFEAdFU

Using a procedure identical as in Example 2, a reaction between phosphorylated 2,3'-anhydro-2'-dideoxy-5-fluorouridine (0.88 mmol, 0.200 g) and 2-fluoroethylamine hydrochloride (263 mg; 2.64 mmol) was performed. Following chromatographic purification, a product (MFEAdFU) was obtained with 34% yield.

¹H NMR (DMSO-d$_6$) δ: 2.56-2.75 (m, 2H, H-2', H-2"), 3.00-3.23 (m, 2H, N—CH$_2$—C), 3.87-4.20 (m, 1H, H-4'), 4.54 (m, 2H, H-5', H-5"), 4.68-4.79 (m, 2H, N—C—CH$_2$), 5.54 (m, 1H, H-3'), 6.04 (pseudo t, J=6.2 Hz, 1H, H-1'), 6.72 (m, 1H, NH—C—C), 7.24, 7.28 (d, 2H, J 8.6 Hz, 4-ClPh), 7.44, 7.48 (d, 2H, J=8.6 Hz, 4-ClPh), 8.15, 8.18 (d, 1H, J=5.6 Hz, H-6), 11.99 (br s, 1H, 3-NH).

¹³C NMR (DMSO-d$_6$) δ: 33.12, 45.51, 63.89, 77.12, 82.48, 83.24, 87.58, 121.74, 125.97 (d, J$_{C-F}$=37.3 Hz), 128.12, 131.07, 143.74 (d, J$_{C-F}$=232.3 Hz), 149.05, 151.48, 162.99 (d, J$_{C-F}$=26.0 Hz).

¹⁹F NMR (DMSO-d$_6$) δ: −71.17 (m, 1F), −158.19 (m, 1F).
³¹P NMR (DMSO-d$_6$) δ 5.96; 6.01.
MS-ESI m/z: 464, 466 [M+H]⁺; 486, 488 [M+Na]⁺; 502, 504 [M+K]⁺; 462, 464 [M−H]⁻; 498, 500, 502 [M+Cl]⁻.

The invention claimed is:

1. 2,3'-Anhydro-2'-deoxy-5-fluorouridine derivatives of general formula 1

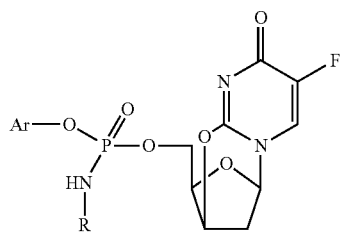

(1)

where:
— Ar is a phenyl, 4-chlorophenyl, 1-naphthyl, 2-naphthyl group or a phenyl group substituted at position para, meta or ortho: with one F, Cl, Br or I atom, an alkyl substituent containing from 1 to 12 carbon atoms, an alkoxy group containing from 1 to 12 carbon atoms, a nitro or trifluoromethyl group; or a phenyl group substituted at any position with two identical or different substituents of the group of F, Cl, Br or I, an alkyl substituent containing from 1 to 12 carbon atoms, an alkoxy group containing from 1 to 12 carbon atoms, a nitro or trifluoromethyl group; and
— R is a trifluoromethyl, 2,2,2-trifluoroethyl, difluoromethyl, perfluoroethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1,2,2-tetrafluoroethyl, 1,2,2,2-tetrafluoroethyl group.

2. A process for the preparation of 2,3'-anhydro-2'-deoxy-5-fluorouridine derivatives of general formula 1

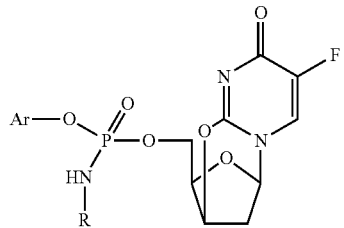

(1)

where Ar and R are as defined in claim 1, wherein the process comprises a reaction of a triazolide of general formula 2

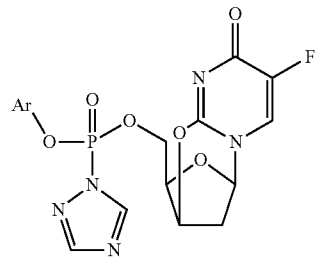

(2)

where Ar is a phenyl, 4-chlorophenyl, 1-naphthyl, 2-naphthyl group or a phenyl group substituted at position para, meta or ortho: with one F, Cl, Br or I atom, an alkyl substituent containing from 1 to 12 carbon atoms, an alkoxy group containing from 1 to 12 carbon atoms, a nitro or trifluoromethyl group; or a phenyl group substituted at any position with two identical or different substituents of the group of F, Cl, Br or I, an alkyl substituent containing from 1 to 12 carbon atoms, an alkoxy group containing from 1 to 12 carbon atoms, a nitro or trifluoromethyl group;
with fluorinated amines of general formula 3

R—NH$_2$     (3)

where R is a trifluoromethyl, 2,2,2-trifluoroethyl, difluoromethyl, perfluoroethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 1,1,2,2-tetrafluoroethyl, 1,2,2,2-tetrafluoroethyl group,
or amine salt of general formula 4

R—NH$_3^+$X⁻     (4)

where R is as defined above, and X⁻ is an inorganic anion of the group Cl⁻, Br⁻, HSO$_4^-$, SO$_4^{2-}$, NO$_3^-$,
in the presence of aliphatic amines.

3. A method for treating at least one cancer selected from the group consisting of breast cancer, cervical cancer, lung cancer and nasopharynx cancer, comprising administering to a patient inflicted with the cancer a therapeutic formulation comprising 2,3'-anhydro-2'-deoxy-5-fluorouridine derivatives of general formula 1

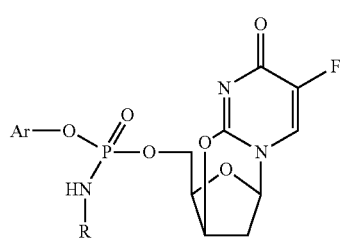

(1)

where Ar is para-chlorophenyl or phenyl and R is —CF$_3$ or —CF$_2$—CF$_3$.

4. The method according to claim 3, wherein the cancer is breast cancer and the 2,3'-anhydro-2'-deoxy-5-fluorouridine derivative of general formula 1 is 2,3'-anhydro-2'-deoxy-5-fluorouridine 5'-[N-(2,2,2-trifluoroethyl)-O-(4-chlorophenyl)]phosphate.

5. The method according to claim 3, wherein the cancer is cervical cancer and the 2,3'-anhydro-2'-deoxy-5-fluorouridine derivative of general formula 1 is 2,3'-anhydro-2'-deoxy-5-fluorouridine 5'-[N-(2,2,2-trifluoroethyl)-O-(4-chlorophenyl)]phosphate.

6. The method according to claim 3, wherein the cancer is lung cancer and the 2,3'-anhydro-2'-deoxy-5-fluorouridine derivative of general formula 1 is 2,3'-anhydro-2'-deoxy-5-fluorouridine 5'-[N-(2,2,2-trifluoroethyl)-O-(4-chlorophenyl)]phosphate.

7. The method according to claim 3, wherein the cancer is nasopharynx cancer and the 2,3'-anhydro-2'-deoxy-5-fluorouridine derivative of general formula 1 is 2,3'-anhydro-2'-deoxy-5-fluorouridine 5'-[N-(2,2,2-trifluoroethyl)-O-(4-chlorophenyl)]phosphate.

\* \* \* \* \*